(12) United States Patent
Chandran et al.

(10) Patent No.: US 8,752,551 B2
(45) Date of Patent: *Jun. 17, 2014

(54) HYBRID VENTILATION MASK WITH NASAL INTERFACE AND METHOD FOR CONFIGURING SUCH A MASK

(75) Inventors: Sanjay Chandran, Boca Raton, FL (US); Louis Javier Collazo, Pompano Beach, FL (US)

(73) Assignee: Respcare, Icn., Coconut Creek, FL (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/238,201

(22) Filed: Sep. 21, 2011

(65) Prior Publication Data

US 2012/0012114 A1    Jan. 19, 2012

Related U.S. Application Data

(63) Continuation of application No. 11/175,683, filed on Jul. 6, 2005, now Pat. No. 8,042,539.

(60) Provisional application No. 60/634,802, filed on Dec. 10, 2004.

(51) Int. Cl.
*A61M 16/06*    (2006.01)

(52) U.S. Cl.
CPC ... *A61M 16/0666* (2013.01); *A61M 2016/0605* (2013.01); *A61M 16/06* (2013.01)
USPC ............. 128/206.28; 128/206.21; 128/206.24

(58) Field of Classification Search
CPC ..... A61M 15/08; A61M 15/00; A61M 16/00; A61M 16/06; A61M 16/0666; A61M 2015/08; A61M 2016/0666; A61M 2016/0605; A61M 2016/06; A61M 2016/00; A61M 2016/0672; A61M 2016/0616; A61M 2210/0618

USPC ............. 128/200.24, 205.25, 206.21, 206.23, 128/206.24
See application file for complete search history.

(56) References Cited

U.S. PATENT DOCUMENTS

| 2,433,565 A | 12/1947 | Korman |
| 4,248,218 A | 2/1981 | Fischer |

(Continued)

FOREIGN PATENT DOCUMENTS

| DE | 3719009 A1 | 12/1988 |
| DE | 19944242 A | 3/2001 |

(Continued)

OTHER PUBLICATIONS

Respironics Co.—Mask Family—http://masksfamily.respironics.com/ viewed on Jul. 24, 2006.

(Continued)

*Primary Examiner* — Annettte Dixon
(74) *Attorney, Agent, or Firm* — Maier & Maier, PLLC

(57) ABSTRACT

A nasal ventilation interface and method for providing nasal ventilation to a patient includes a hybrid face mask, covering only the mouth, coupled with removable nasal inserts extending from the upper surface of the mask. The nasal interface has modular, removable, and disposable nasal pillows connecting the upper surface of the mouth-portion of the mask to the user's nares. Each part of the hybrid mask is modular and can be formed in various shapes and sizes. The ventilation interface has differing gas line entry ports and can be shallow with a relatively deep soft facial interface or deep with a relatively shallow facial interface. In either case, the upper surface receives the nasal interface. The upper surface can have a removable ceiling in which is defined a nasal interface connector. The nasal interface can be integral with a removable ceiling. The entire hybrid mask can be made in one piece.

18 Claims, 6 Drawing Sheets

(56) References Cited

U.S. PATENT DOCUMENTS

| | | | |
|---|---|---|---|
| 4,263,908 A | 4/1981 | Mizerak | |
| 4,782,832 A | 11/1988 | Trimble et al. | |
| 5,269,296 A * | 12/1993 | Landis | 128/207.18 |
| 5,570,684 A | 11/1996 | Behr | |
| 5,647,357 A * | 7/1997 | Barnett et al. | 128/206.24 |
| 5,724,965 A | 3/1998 | Handke et al. | |
| 5,921,239 A | 7/1999 | McCall et al. | |
| 6,123,071 A * | 9/2000 | Berthon-Jones et al. | 128/204.18 |
| 6,273,087 B1 * | 8/2001 | Boussignac et al. | 128/204.22 |
| 6,412,487 B1 | 7/2002 | Gunaratnam et al. | |
| 6,427,694 B1 | 8/2002 | Hecker et al. | |
| 6,431,172 B1 | 8/2002 | Bordewick | |
| 6,581,601 B2 | 6/2003 | Ziaee | |
| 6,595,214 B1 | 7/2003 | Hecker et al. | |
| 6,595,215 B2 | 7/2003 | Wood | |
| 6,626,177 B1 | 9/2003 | Ziaee | |
| 6,644,315 B2 | 11/2003 | Ziaee | |
| 6,776,162 B2 | 8/2004 | Wood | |
| 6,807,967 B2 | 10/2004 | Wood | |
| 6,817,362 B2 | 11/2004 | Gelinas et al. | |
| 6,860,268 B2 | 3/2005 | Bohn et al. | |
| 7,178,525 B2 | 2/2007 | Matula, Jr. et al. | |
| 7,191,781 B2 | 3/2007 | Wood | |
| 7,219,669 B1 * | 5/2007 | Lovell et al. | 128/206.24 |
| 7,578,294 B2 | 8/2009 | Pierro et al. | |
| 7,762,258 B2 | 7/2010 | Zollinger et al. | |
| 8,042,539 B2 * | 10/2011 | Chandran et al. | 128/206.28 |
| 2001/0020474 A1 | 9/2001 | Hecker et al. | |
| 2002/0148472 A1 * | 10/2002 | Barnett et al. | 128/206.24 |
| 2007/0272249 A1 * | 11/2007 | Chandran et al. | 128/206.28 |
| 2009/0032026 A1 * | 2/2009 | Price et al. | 128/207.11 |

FOREIGN PATENT DOCUMENTS

| | | |
|---|---|---|
| EP | 0658356 A2 | 6/1995 |
| GB | 532214 A | 1/1941 |
| GB | 2368533 A | 5/2002 |
| WO | 01/97892 A1 | 12/2001 |
| WO | 2005/063328 A1 | 7/2005 |
| WO | 2008040050 A1 | 4/2008 |

OTHER PUBLICATIONS

Hans Rudoply Inc.—Mask Products—http://www.rudolphkc.com/list_all.php viewed on Jul. 24, 2006.

International Search Report from International Patent Application No. PCT/US06/20145 dated Dec. 1, 2006—1 page.

* cited by examiner

HYBRID VENTILATION MASK WITH NASAL INTERFACE AND METHOD FOR CONFIGURING SUCH A MASK

CROSS-REFERENCE TO RELATED APPLICATION

This application is a continuation of U.S. patent application Ser. No. 11/175,683, filed Jul. 6, 2005, now U.S. Pat. No. 8,042,539, which claims priority, under 35 U.S.C. §119, to U.S. Provisional Patent Application No. 60/634,802 filed Dec. 10, 2004, the entire disclosure of which is incorporated by reference in its entirety.

STATEMENT REGARDING FEDERALLY SPONSORED RESEARCH OR DEVELOPMENT n/a

FIELD OF THE INVENTION

The present invention lies in the field of respiration and/or ventilation masks. In particular, the present invention is directed to a hybrid mouth/nasal ventilation mask with a removable nasal ventilation interface, the mask to be connected to a source of ventilation for a patient, and to a method for configuring such a mask.

BACKGROUND OF THE INVENTION

Obstructive sleep apnea syndrome (commonly referred to as obstructive sleep apnea, sleep apnea syndrome, and/or sleep apnea) is a medical condition that includes repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage tends to narrow due to the relaxation of the muscles. In those individuals having a relatively normal-sized throat passage, the narrowed throat passage remains open enough to permit the adequate amount of oxygen to flow into the lungs. However, in those individuals having a relatively smaller-sized throat passage, the narrowed throat passage prohibits the adequate amount of oxygen from flowing into the lungs. Additionally, a nasal obstruction, such as a relatively large tongue, and/or certain shapes of the palate and/or the jaw of the individual, further prohibit the adequate amount of oxygen from flowing into the lungs.

An individual having the above-discussed conditions can stop breathing for one or more prolonged periods of time (e.g., 10 seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and/or depression.

Other medical conditions can also prevent individuals, including adults and infants, from receiving the adequate amount of oxygen into the lungs. For example, an infant who is born prematurely can have lungs that are not developed to an extent necessary to receive the adequate amount of oxygen. Further, prior to, during, and/or subsequent to certain medical procedures and/or medical treatments, an individual can be unable to receive the adequate amount of oxygen. Under these circumstances, it is known to use a ventilation interface to apply a positive pressure to the throat of the individual, thereby permitting the adequate amount of oxygen to flow into the lungs. In the known ventilation interface, oxygen and/or room air containing oxygen is delivered through the mouth and/or nose of the individual. Existing types of positive pressure applied by the known ventilation interface include continuous positive airway pressure (CPAP), in which a positive pressure is maintained in the throat passage throughout a respiratory cycle, bi-level positive airway pressure (BiPAP), in which a relatively high positive pressure is maintained during inspiration and a relatively low positive pressure is maintained during expiration, and intermittent mechanical positive pressure ventilation (IPPV) in which a positive pressure is applied when apnea is sensed (i.e., the positive airway pressure is applied intermittently or non-continuously). Some of these technologies are discussed, for example, in U.S. Provisional Patent Application No. 60/645,672.

One conventional ventilation interface for the application of positive pressure includes a face mask that covers both the nose and the mouth. See, for example, U.S. Pat. No. 4,263,908 to Mizerak and U.S. Pat. No. 6,123,071 to Berthon-Jones et al. Other face masks include configurations that cover only the nose or cover only the mouth. Standard masks have air supplied under pressure and use headgear or harnesses configured at least with what is referred to as a lip strap, thereby preventing air to escape from the user's mouth. Such a strap is positioned level with the patient's lips and wraps circumferentially around the patient's head from one side of the mask to the other. To keep the supply of positive gas pressure and to maintain the required seal that prevents the gas supply from leaking, a force must be applied by the harness to the head of the individual. As a result, the harness is generally uncomfortable to wear, particularly when sleeping. The applied pressure often results in undesirable irritation and sores caused by movement of the mask and harness during periods of both wakefulness and sleep. Further, the required seal is generally difficult to maintain when the mask and harness is moved.

The force that the harness applied to the mask against the face also applies an undesirable pressure to the sinus area adjacent to the nose, causing the nasal sinus airways to narrow. This narrowing causes an increase in the velocity of flow through the upper anatomical airways and a decrease in the lateral pressure against the nasal mucosal wall. Additionally, if the tubing between the mask and the gas supply unit folds undesirably, this problem will be exacerbated. The above-discussed combination of increased flow velocity and decreased pressure results in the removal of moisture from the mucosal walls during inspiration and may cause an undesirable drying and a burning sensation within the nares. As a result, the individual may remove the mask to alleviate these discomforts, consequently discontinuing the beneficial application of the positive pressure. Such increased air flow velocity and decreased pressure deteriorate the laminar flow between the air input and output portions of the conventional mask.

A patient's most common complaint regarding prior art ventilation masks is that they cause claustrophobia. Such masks have large headgear that wrap around the entirety of the user's head and cover area of the face including the periphery of both the nose and the mouth. Therefore, the user feels as if they are in a tunnel, which feeling is uncomfortable to the user.

Some prior art masks include nasal pillows, for example, U.S. Pat. No. 4,782,832 to Trimble et al. and U.S. Pat. No. 6,431,172 to Bordewick. However, such masks are not comfortable and do not fit in the most efficient manner.

It would be desirable, therefore, to provide a nasal breathing mask that reduces the feeling of claustrophobia, improves the fit and comfort, and provides an economical and sanitary solution to problems with conventional nasal breathing masks

SUMMARY OF THE INVENTION

The present invention addresses the deficiencies of the art with respect to ventilation, in particular, ventilation masks, and provides a novel and non-obvious method and system for providing ventilation to a patient.

In an exemplary embodiment of the invention, a conventional ventilation interface for the application of positive air pressures including a face mask that covers only the mouth and is coupled with removable nasal inserts that extend from the upper surface of the mask. This mask is referred to herein as a hybrid mask.

The hybrid mask according to the invention removes almost all of the upper half of prior art masks that previously covered the patient's nose. All that is provided for the nasal interface is what are referred to as nasal pillows. These pillows are disposed between the upper surface of the mouth-portion of the mask and the user's nares. Such masks eliminate the requirement of large prior art headgear—only side straps are needed. Therefore, the user has no obstruction between the eyes and does not have the closed-in feeling.

By providing a removable nasal interface, which is also disposable, the user not only has the ability to throw away the nasal interface when it is used or unsanitary but also has the ability to customize the shape and size of the nasal interface to the user's particular facial shape.

It is beneficial if the parts of the hybrid mask are modular and various sizes for each piece are provided. The ventilation interface can have various configurations for gas line entry ports (e.g., front sides, front center, bottom) to accommodate the user's preferences. The gas line entry ports can even be at the facial interface (e.g., at the sides or bottom thereof) or at the nasal interface (e.g., at one or more sides of the nasal pillows to form a nasal cannula that is also fluidically connected to the interior of the oral breathing chamber). The ventilation interface can be shallow with a relatively deep soft facial interface or it can be deep with a relatively shallow facial interface. In the former case, the facial interface defines the area on its upper surface for receiving a nasal interface and, in the latter case, the ventilation interface defines the upper surface for receiving the nasal interface. The nasal interface can take the form of two nasal pillows (connected to one another or not) that are inserted into ports in the upper surface. Alternatively, the upper surface can have a removable ceiling in which is defined the nasal interface connector. In another variation, the nasal interface can be integral with the removable ceiling. In another alternative embodiment, the entire hybrid mask (shell, cushion, and nasal pillows) can be made in one piece.

The overall hybrid mask configuration can have different size cushions and different size nasal pillows. These can be assembled together to offer a very wide range of sizing options.

With regard to the nasal interface according to the present invention, it is, preferably, a nasal pillow style that can come in different sizes. The pillow may also be a "volcano" style (tapered nasal insert with no specific sealing detail), a nasal insert with an exterior sealing bead, flange, or other (like one manufactured by Innomed Technologies, Inc.), or some other style.

In one configuration, both nasal pillows are integrated into one part that has a standard orientation. Alternatively, the nasal pillows may be two individual components. The pillows can be trimmed apart from each other to allow a user to adjust the configuration of each individual pillow or to use two different sized pillows if either of these was desired. The nasal pillows are of a soft material for increased comfort and sealing. The material may be rigid.

The nasal pillows assemble by squeezing and inserting the pillows into holes in the facial interface (also referred to as the cushion) of the mask, which allows the pillows to be removable. The pillows could also assemble by various other methods. For example, the pillows could assemble to the ventilation interface, which is also referred to as the shell.

The pillows may assemble in a non-removable manner such as welding, bonding, etc. or they may be molded into one of the other main components, such as the cushion or shell.

The pillows may be attached or captured by a secondary piece (such as a base, cover, or ring) that, then, attaches to the remainder of the mask.

The pillows may be integrated into another component, such as a nasal cannula or be replaced by another interface, such as a separate nasal mask. This component may or may not be assembled to the oral section of the mask. For example, the pillows may bypass the oral section of the mask. This component may receive the fluid supply directly from the oral section or it could have a separate supply from another section of the circuit.

The pillows may be of a pliable material and may have molded-in geometry or a secondary piece that allows the internal diameter opening to be adjusted and set to multiple sizes.

In an oral-only application, the nasal pillows may not be included in the mask geometry. A secondary nasal plug may be used, which may be attached to the mask or be a separate part. The hole(s) for the nasal pillows may plugged by a secondary piece. A secondary nasal plug may be needed, which may be attached to the mask or be a separate part.

The cushion or facial interface can be made in different sizes. The preferred configuration is a one part construction that utilizes a double membrane style for the cushioning and sealing. The cushion may be made up of several parts. The cushioning and sealing may be accomplished through a single membrane or multiple membranes. It could also be accomplished using a gel style cushion or some other style cushion.

The cushion may be made of a soft material for increased comfort and sealing. Alternatively, the material may be rigid. The cushion may be a pliable material and may have molded-in geometry or secondary piece that allows the opening, cushioning, or sealing area to be adjusted and set to multiple sizes.

The cushion can assemble to the shell by a press-fit. This configuration allows the cushion to be removable. The cushion may also assemble by various other methods. For example, the cushion may assemble in a non-removable manner such as welding, bonding, etc. or it may be molded into one of the other main components, such as the shell. The cushion may be attached or be captured by a secondary piece (such as a base, cover, or ring) that, then, attaches to the rest of the mask.

The preferred embodiment of the cushion profile is an oval shape that seals around the mouth. But, the profile may take any shape (rectangular, square, triangular, circle, irregular, etc.). The cushion could also seal on or inside the mouth.

With regard to the shell or ventilation interface, the preferred configuration has one size that accepts the different size cushions and nasal pillows. The shell, however, may be of multiple sizes. The preferred shell configuration is a one part construction. However, the shell may be made up of several parts.

Preferably, the shell is made of a rigid material. Alternatively, the material may be soft. The shell may be a pliable material and may have molded-in geometry or secondary piece that allows it to be adjusted and set to multiple sizes.

A preferred configuration of the shell interfaces with a swiveling elbow connector to attach the mask to the ventilation circuit. Such a connector may or may not be removable. The interface may be a single connection or have multiple connection points. The interface may occur at the front, top, bottom, or sides of the shell, cushion, or other component.

The mask of the present invention has exhalation ports, which are molded into the front of the shell. The exhalation ports may be located at the front, top, bottom, or sides of the shell, cushion, or other component. The preferred configuration for the exhalation ports are multiple, small, tapered holes. But, the exhalation ports may be any style, profile, or number. The exhalation ports may be plugged or may not be included at all, for example, for ventilation applications.

The mask of the present invention includes a chin support flap. This flap may be part of the cushion or shell, or it may be a separate component. The chin flap supports the chin and limits a user's ability to open his/her mouth because the act of opening one's mouth increases the likelihood of creating a leak in the oral perimeter seal. Such a chin flap may be integral to the sealing area. Alternatively, the chin flap may be outside the sealing area, in which case the user can be allowed to trim away the chin flap if it was not desired and such elimination would not affect the seal. Such a configuration would provide a trimming guide detail, such as a cut-line or a raised guide.

The headgear for the mask of the present invention may be used to support the mask and create and/or assist the seal. The headgear may attach to the shell, the cushion, or another component. The headgear may be a molded-in feature of the shell, cushion, or other component.

Additional ports may be integrated into the shell, cushion, or other component for miscellaneous purposes such as oxygen entrainment.

Applications for the hybrid mask of the present invention include homecare, hospital care, critical care, CPAP, BiPAP, and ventilation. The hybrid mask may be used to provide therapy similar to a full facemask, oral/nasal mask, nasal mask, nasal cannula, or oral mask.

BRIEF DESCRIPTION OF THE DRAWINGS

Advantages of embodiments the present invention will be apparent from the following detailed description of the preferred embodiments thereof, which description should be considered in conjunction with the accompanying drawings in which.

DETAILED DESCRIPTION OF THE PREFERRED EMBODIMENTS

Figure 2:
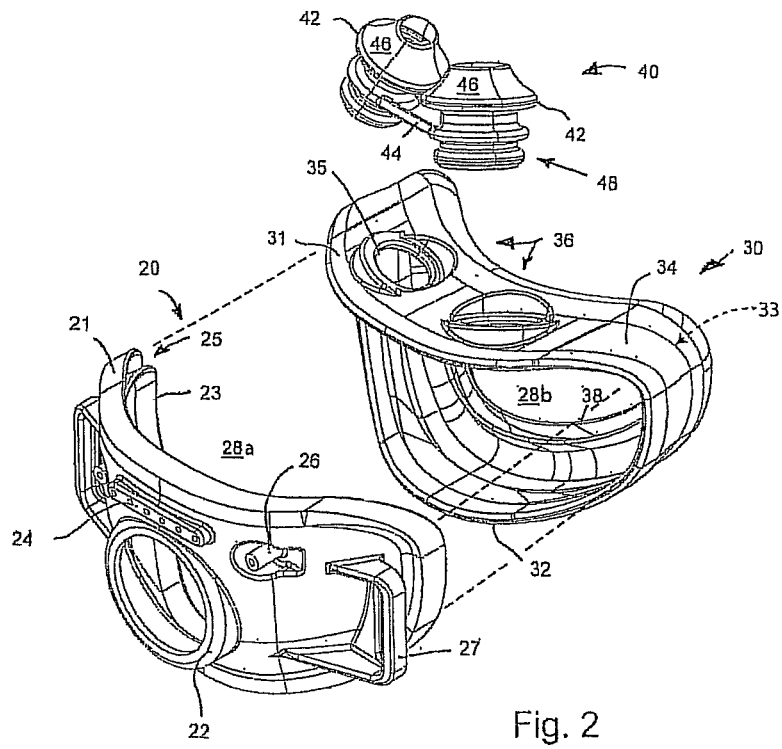
FIG. 2 is an exploded perspective view of the nasal interface of FIG. 1.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

Figure 1:
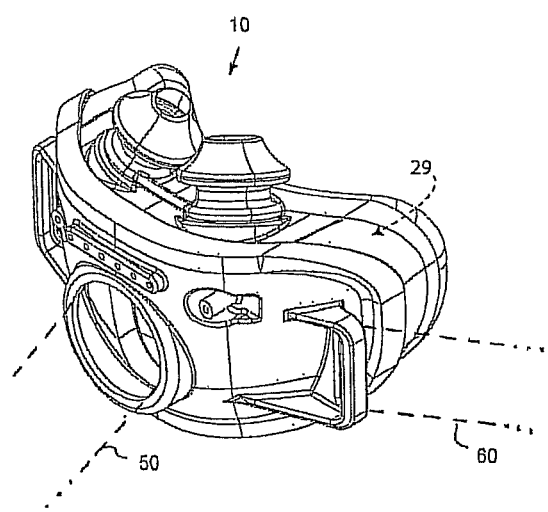
FIG. 1 is a perspective view from above and to the side of an exemplary embodiment of the mask according to the invention.
Figure 3:
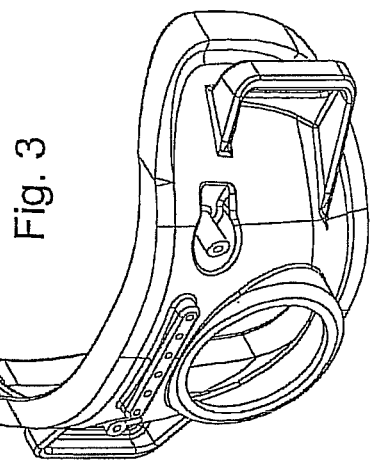
FIG. 3 is a perspective view from above and to the side of a ventilation interface of the mask of FIG. 1.
Figure 5:
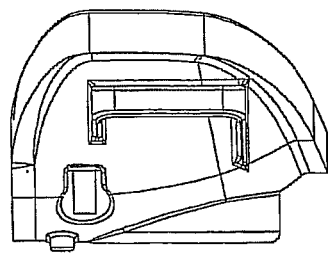
FIG. 5 is a side elevational view of the ventilation interface of FIG. 3.
Figure 6:
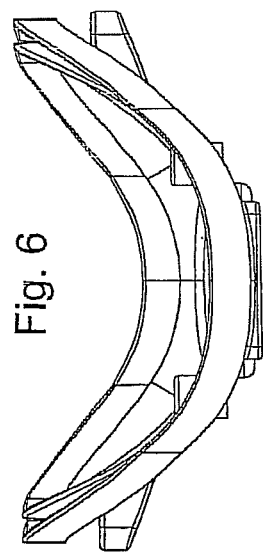
FIG. 6 is a plan view of the ventilation interface of FIG. 3.
Figure 4:
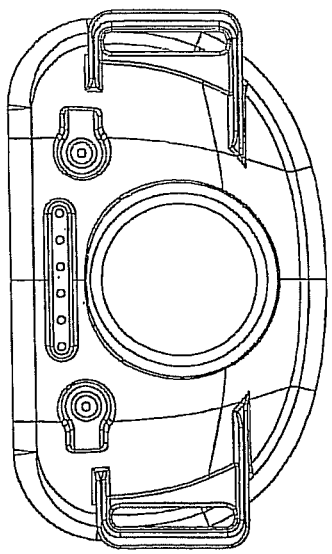
FIG. 4 is a front elevational view of the ventilation interface of FIG. 3.

Referring now to the figures of the drawings in detail and first, particularly to FIGS. 1 and 2 thereof, there is shown an exemplary embodiment of the present hybrid mask invention for applying positive air pressure. In the embodiment of FIGS. 1 and 2, the hybrid mask 10 has three significant parts: a ventilation interface 20, a cushioned facial interface 30, and a nasal interface 40. As will be described in further detail below, various aspects of these three parts can be moved and/or interchanged.

The mask 10 of the present invention completely covers only the mouth of the user. Nonetheless, the mask 10 is still fluidically coupled to the nares of the user through the nasal interface 40. As such, the mask 10 regulates breathing of the user.

The ventilation interface 20 is relatively rigid and hard (as compared to the facial interface 30) and defines a gas entry port 22 to be connected to a gas feeder tube 50, illustrated only diagrammatically in FIG. 1 by dashed lines. The feeder tube 50 is fluidically connected to a source of ventilation, such as a mechanical ventilator described, for example, in U.S. Provisional Patent Application No. 60/645,672 titled "PORTABLE THERAPEUTIC AND DIAGNOSTIC SYSTEM FOR DELIVERING OXYGEN TO A PATIENT AND METHOD FOR OXYGEN DELIVERY." It is noted that the large central, circular entry port 22 does not need to be shaped, sized, or located as shown in FIGS. 1 to 4 and 6. Alternatively, a port 22 can be located on either or both sides of a center of the ventilation interface 20 or on the bottom of the ventilation interface 20.

When a headgear 60 is attached to any part of the mask 20, 30, 40 and is, then, placed on a user's head, the mask is pressed against the face of the user to effect a substantially gas-tight seal. The headgear 60 is illustrated by dashed lines in FIG. 1 and attaches, in the preferred embodiment, to the hard shell of the ventilation interface 20 by stirrups 27. The headgear 60 is adjustable and, in one exemplary embodiment, wraps entirely around the user's head to help maintain the substantially gas-tight seal between the user's face and the facial interface 30 of the mask 10. As used herein, substantially gas-tight is defined as a connection that is just tight enough to not degrade performance of a particular application in which the mask of the present invention is used.

The ventilation interface 20 is configured with at least one exhalation port 24. The exhalation port 24 can take any shape or have any size and can be in any number. For example, the port 24 can be located anywhere on the ventilation interface 20 or the facial interface 30. The port 24 can be in the form of bleed nipples, variable bleed ports, or diffusers. Preferably, however, the exhalation port 24 is adjustable, for example, with a non-illustrated slide, dial, or louver, so that the user can adjust the pressure of gas that is to be delivered. Additional ports 26 can be provided, for example, to deliver a gas different and/or separate from the gas delivered through the gas feeder tube 50 (e.g., oxygen in addition to air).

The ventilation interface 20 is connected to the facial interface 30 in a removable but secure and gas-tight manner. The two interfaces 20, 30 can have any kind of securing connection—they can even be fixedly connected to one another if desired. However, the preferred embodiment is shown in FIGS. 1 and 2, in which the ventilation interface 20 has two circumferential, rearwardly projecting walls 21, 23 defining a groove or gap 25 therebetween. In such a configuration, the ventilation interface 20 can be easily separated from the facial interface 30 for cleaning and/or replacement, for example. This connection can also be reversed so that the ventilation interface 20 has a trailing edge 103 and the facial interface 30 has two leading, forwardly projecting circumferential walls 104 and 105. The former connection is preferred because the relatively softer facial interface 30 easily inserts into the relatively harder ventilation interface 20 and holds securely while providing a gas-tight connection. Another benefit to the modularity created by such a connection is that different shaped ventilation interfaces 20 or facial interfaces 30 can be easily connected to one another to, in the former case, accommodate different shaped gas feeder tubes 50 or gas feeder tube connection assemblies or, in the latter case, to accommodate different shaped or sized facial interfaces 30. The differently shaped and sized facial interfaces 30 can be configured to accommodate, for example, predefined standard facial shapes or, even, customized facial shapes, allowing the user to select a shape that best fits him/her at a fitting location (e.g., doctor's office) and, thereafter, to order that particular, best fitting facial interface 30 from a supplier or pharmacy.

The groove 25 can take any number of shapes and/or sizes. For example, the groove 25 can have a user-face-side and a feeder-tube-facing-side and be formed with a width at the user-face-side smaller than a width at the feeder-tube-facing-side. In other words, the groove can have a somewhat pear-shaped cross-section. In such a configuration, the facial interface 30 has a leading edge or periphery 31 shaped to securely and gas-tightly fit into the groove 25 by having a correspondingly cross-section such that, when inserted into the groove 25, a significant force is needed to remove the leading edge 31 from the groove 25. This connection also is gas-tight.

Figure 9:
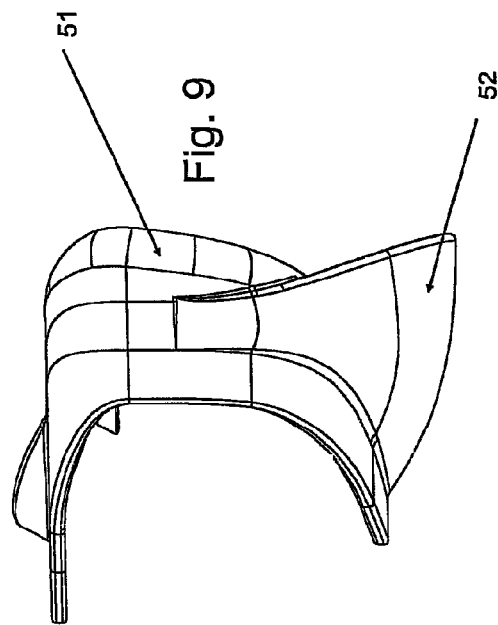
FIG. 9 is a side elevational view of the facial interface of FIG. 7.

The facial interface 30 includes a chin portion 32, an upper surface 34 defining a nasal interface connection 36, and a face-contacting periphery 38. The facial interface 30 is relatively soft compared to the ventilation interface 20 and, therefore, cushions the connection between the user's face and the relatively harder ventilation interface 20. The facial interface 30 is made of a material that feels soft to a user, for example, silicone or another elastomer having a durometer between 20 and 80. As shown in FIG. 9, in one exemplary embodiment of the facial interface 51, the chin portion 52 is shaped to extend around and include at least a part or the entirety of the chin of a user. The perimeter of the facial interface 51 may be triangular, for example, or it may take on any regular or irregular geometric shape. Because the chin portion 52 of the facial interface 51 is soft, it can be manufactured in various anatomical chin geometries to accommodate different facial shapes and, thereby, provide proper and customized sealing for users.

Figure 10:
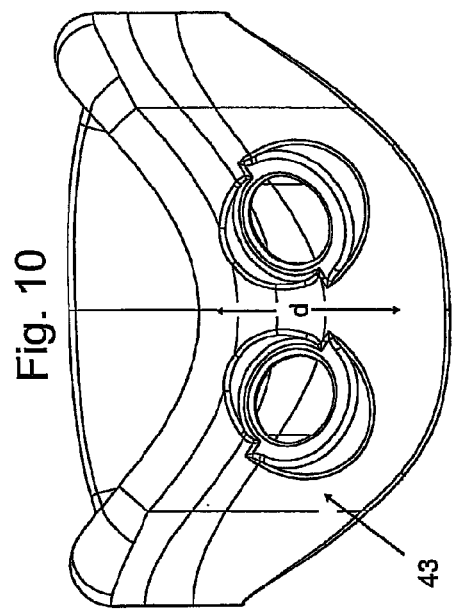
FIG. 10 is a plan view of the facial interface of FIG. 7.
Figure 8:
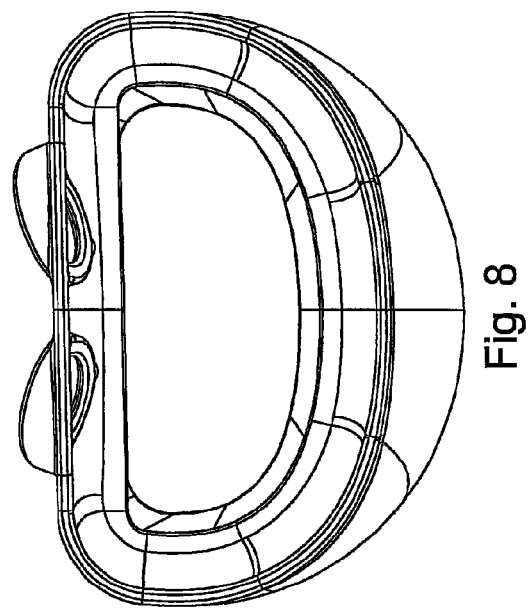
FIG. 8 is a front elevational view of the facial interface of FIG. 7.
Figure 11:
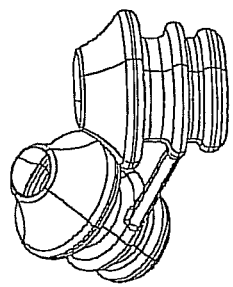
FIG. 11 is a perspective view from above and to the side of a nasal interface of the mask of FIG. 1.
Figure 13:
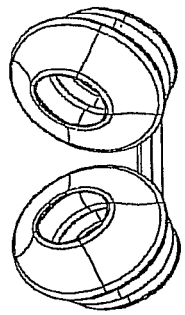
FIG. 13 is a perspective view from above the nasal interface of FIG. 11.

The upper surface 34 of the facial interface 30 defines a nasal interface connection area for receiving the nasal interface 40 in a removable manner. The upper surface 34 has a depth d (see FIG. 10) that is defined by the surface distance between the leading, ventilation-interface-contacting edge 31 and the trailing, face-contacting periphery 38. The upper surface 34 includes the area in which the nasal interface 40 attaches to the facial interface.

Figure 7:
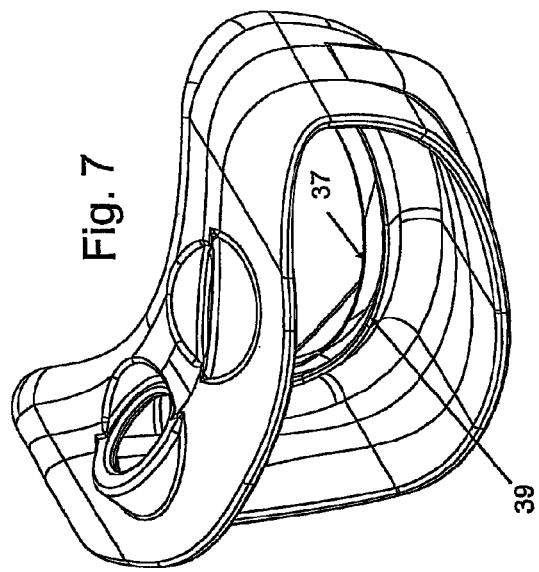
FIG. 7 is a perspective view from above and to the side of a facial interface of the mask of FIG. 1.

The face-contacting periphery 38 preferably has a double-wall configuration, as shown in FIG. 7, to insure a substantially gas-tight seal to the user's face. The walls of the periphery 38 can have the same or different thicknesses. For example, the face-contacting wall 37 can be somewhat thinner than the second wall 39 to provide a lighter "touch" to the user's face.

The nasal interface 40 is attached to the upper surface 34 of the mask so that it can be configured to accommodate a user's nares in the most comfortable manner. In the exemplary embodiment of FIGS. 1, 2, and 7 to 10, the nasal interface 40 is attached, like a nipple to a bottle, to the upper surface 34 of the cushioning facial interface 30. In other words, the soft nasal interface 40 is squeezed and inserted into the upper surface 34 with a form-fitting connection that holds the nasal interface 40 securely, but removably, to the upper surface 34. This form-fitting or form-locking connection is one that connects two elements together due to the shape of the elements themselves, as opposed to a force-locking connection, which locks the elements together by force external to the elements.

Figure 14:
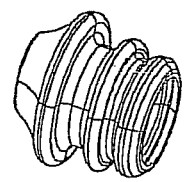
FIG. 14 is a perspective view of a single nasal pillow of the mask of FIG. 1.
Figure 12:
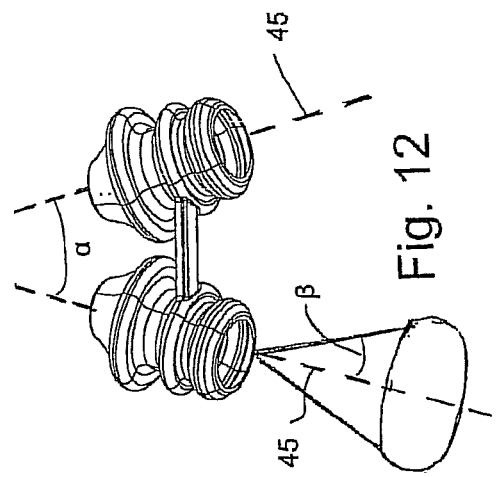
FIG. 12 is a perspective view from the front of the nasal interface of FIG. 11.

Preferably, as shown in FIGS. 1 and 2, the nasal interface 40 has two separate nasal pillows 42 that can be connected to one another by a connecting bar 44 so that insertion of the pillows 42 can occur without one pillow 42 falling from the user's grasp while the other is being inserted into the facial interface 30. The connecting bar 44 also provides the user with the ability to insert the nasal pillows 42 into the facial interface 30 in a proper orientation. As shown in FIGS. 2 and 11 to 13, and especially in FIG. 12, the pillows 42 have central axes 45 that are tilted with respect to one another. Therefore, if the pillows 42 are inserted backwards, the nare-contacting surfaces 46 will be oriented away from the user's nose— clearly indicating an incorrectly positioned nasal interface 40. Alternatively, the nasal pillows 42 can be entirely separate from one another and, in such a configuration, are inserted separately and independently into the upper surface 34. See, e.g., FIG. 14.

In the two nasal pillow configuration, the nasal interface connection 36 can be two portals 36 (as shown in FIGS. 2, 7, 8, and 10). To correspond to the tilted orientation of the nasal pillows 42, the two portals 36 also have tilted orientations. Such tilting not only ensures proper connection of the pillows 42 to the upper surface 34 of the facial interface 30, but it also helps align the axes of the pillows 42 to the corresponding axes of each nare of the user's nose. The orientation of the pillows 42, like other features of the hybrid mask, can be modular and, therefore, tailored to a user for a better fit.

Connection of each nasal pillow 42 to the portals 36 occurs, in the preferred embodiment, by forming the bottom end 48 of each nasal pillow with a first connecting surface and by forming the interior surface 35 with a second connecting surface such that when the two contacting surfaces are positioned together, a gas-tight, removable connection occurs. In particular, the bottom end 48 of each pillow is formed with rings defining at least one groove therebetween, the at least one groove having a given width. Correspondingly, the interior surface 35 of the portals 36 is formed with a thickness that is no greater than the given width. As such, when the nasal pillows 42 are compressed and placed inside the portals 36, the interior surface 35 mates with the rings and sits in the groove to form the substantially gas-tight connection.

The nasal interface 40 can be connected to the portals 36 or to the upper surface 34 in any number of ways. For example, the elastic nasal interface 40 can be secured to the upper surface 34 with a locking mechanism such as a cotter pin, an elastic band, or a C-shaped spring clip. Alternatively, the nasal inserts 20 may be stretched to fit over small protrusions extending upwards from the upper surface 34. In yet another embodiment, the nasal pillows 42 may have threads that screw into corresponding threads in the upper surface 34. Other measures for connecting the nasal pillows 42 or nasal interface 40 to the mask include, for example, forcing the nasal pillows 42 into a recess of the upper surface or applying an adhesive or hook and loop type fasteners.

Figure 16:
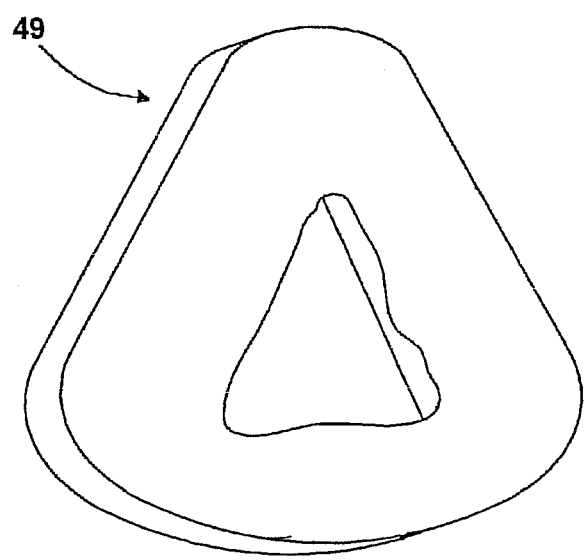
FIG. 16 is a perspective view of a nasal triangle that may be used with the mask of FIG. 1.

The shape of the nasal interface connection 36 (e.g., two portals) does not need to be that shown in FIGS. 2, 7, 8, and 10. Instead, the two portals 36 can be part of an upper surface insert 43, which is defined, for example, by dashed lines in FIG. 10. It is noted that the insert 43 can include a part of the leading, ventilation-interface-contacting edge 31 and/or a part of the trailing, face-contacting periphery 38. The insert 43 can merely include the features shown in FIG. 10, i.e., that portion of the upper surface 34 defining the two portals 36. Alternatively, the two nasal pillows 42 can be integral with the insert 43 and, thereby, allow for a modular nasal interface 40 that can have different shaped and/or angled pillows 42. For example, the modular nasal interface 40 can have nasal pillow axes 45 (see FIG. 12) that are oriented in any angle α, or at any angle β with respect to the axes 45. The presence of a large opening for accommodating the upper surface insert 43 allows for the possibility of replacing a pair of nasal pillows 42 with what is referred to as a nasal triangle 49 (see FIG. 16). A nasal triangle is a mask unit that entirely surrounds the user's nose and seals against the upper lip, cheeks, and nose bridge of the user.

Preferably, the nasal interface 40 is removable and, therefore, disposable. In such a configuration, the user can periodically replace the nasal interface 40 due to wear or sanitary conditions. The removable nasal interface 40 may be configured similar to the nasal inserts disclosed in U.S. Pat. Nos. 6,807,967, 6,776,162, and 6,595,215 to Wood, the disclosures of which are hereby incorporated by reference in their entirety. These patents are assigned to Innomed Technologies, Inc.

The nasal interface 40 according to the present invention provides increased comfort and functionality, and, because they are removable—i.e., disposable—they provide an improved economical and sanitary solution to problems with conventional nasal breathing masks.

Another alternative embodiment can have the ventilation interface 20 and the facial interface 30 be a single integral part. Such a part can be manufactured with two or more different materials (for example, by co-extrusion) or it can be a single part having a uniform or non-uniform density (the non-uniform density creating different levels of stiffness in the mask). This part is especially easy to manufacture if a removable ceiling insert 43 includes the nasal interface 40. The nasal interface 40 can also be integral with the two other interfaces 20, 30 to form a one-piece mask having nasal pillows on the upper surface thereof. Any two of these three parts can be integral and then attached with the third part (i.e., 20 and 30 integral, 30 and 40 integral, or 20 and 40 integral). With all of the possible variations, the differing parts can form a multi-part kit that a user can put together to form a very customized and, therefore, comfortable mask.

The ventilation interface 20 includes a first chamber 28a defined therein and the facial interface 30 includes a second chamber 28b defined by a gas exit 33 of the facial interface 30. When connected together to form the mask 10, the ventilation interface 20 and the facial interface 30 are shaped to provide an air reservoir 29 (shown in FIG. 1) in and around the mouth of the user. Accordingly, the rear-most edge (face-contacting periphery 38) of the facial interface 30 forms the only contact point between the two components of the mask 20, 30 and the face of the user. These two components of the mask 20, 30 along with the nasal interface 40 are sized and shaped to facilitate producing laminar flow between the feeder tube 50, the gas entry port 22, the air reservoir 29, the nasal interface 40, the ventilation interface 20, the facial interface 30 and/or the at least one exhalation port 24. Preferably, the exhalation port 24 is adjustable so that the user can set a given air pressure prescribed by a physician. Otherwise, the user can simply adjust the air pressure for optimized comfort. While the mask 10 can be used with a conventional sealing gel to help create the proper seal around the cushioned perimeter of the facial interface 30, such a gel is not necessary.

Figure 15:
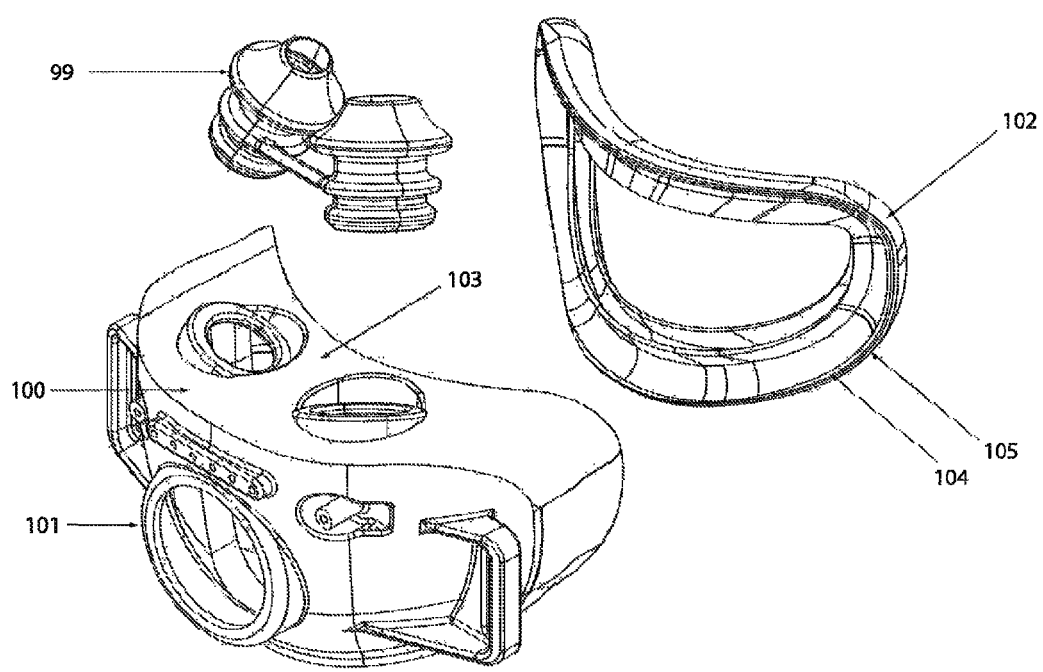
FIG. 15 is another exemplary exploded perspective view of the mask.

In the exemplary embodiment of FIGS. 1 to 10, the walls 21, 23 of the ventilation interface 20 are relatively short and the depth d of the upper surface 34 is relatively long. In an alternative embodiment, as shown in FIG. 15, the hard shell of the ventilation interface 101 can extend rearward towards the users face (but not all of the way to the user's face) and encompass the entire area for receiving the nasal interface 99 therein. In such a configuration, the nasal interface 99 is attached to an upper surface 100 with a depth on the ventilation interface 101 in any way that it could be attached to the upper surface 34 of the facial interface 30 as set forth with regard to the first embodiment. In the alternative configuration with the extended ventilation interface 101, the facial interface 102 takes the shape of a grommet or a relatively ring-shaped gasket that is attached to the rear-most edge of the ventilation interface 101.

Still generally referring to FIGS. 1 and 2, an exemplary conventional nasal breathing mask such as those disclosed in U.S. Pat. Nos. 6,427,694 and 6,595,214 to Hecker et al., or the V.I.P 7600 Vmask Oro-Nasal Mask produced by Hans Rudolph, Inc., or similar masks may be configured with the removable nasal interface 40 of the present invention.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A respiration assist mask comprising:
    a ventilation interface defining a gas entry port to be connected to a positive gas pressure source supplying a gas to said ventilation interface;
    a cushioned facial interface comprising a non-face contacting periphery comprised of a bottom wall, two side walls, and a top wall, a face contacting periphery extending from the non-face contacting periphery, wherein the top wall has an upper surface that has at least one orifice defined on said upper surface of the non-face contacting periphery; and
    a nasal interface coupled with said at least one orifice, the nasal interface having a nasal interface gas exit that is external to the cushioned facial interface;
    wherein the cushioned facial interface is in fluid communication with the ventilation interface and the nasal interface.

2. The mask according to claim 1, wherein said ventilation interface comprises at least two walls extending about a periphery of said ventilation interface wherein a first wall is positioned a distance away from a second wall such that a groove is defined therebetween; and
    wherein said cushioned facial interface comprises an edge extending from said cushioned facial interface, said edge is sized and shaped to be positioned within said groove to facilitate removably coupling said cushioned facial interface to said ventilation interface.

3. The mask according to claim 1, wherein said mask has at least one exhalation port.

4. The mask according to claim 1, wherein said facial interface is removably coupled to said ventilation interface.

5. The mask according to claim 1, wherein said nasal interface is removably coupled to said upper surface.

6. The mask according to claim 1, wherein any two of said nasal interface, said ventilation interface, and said facial interface are integral and a remaining one of said nasal interface, said ventilation interface, and said facial interface is removably attached to said two integral other interfaces.

7. The mask according to claim 1, wherein said facial interface is made of a flexible material.

8. The mask according to claim 1, wherein said nasal interface is made of a flexible material.

9. The mask according to claim 1, further comprising a gas exit defined in said facial interface, said gas exit is shaped to completely surround only the mouth of the user.

10. The mask according to claim 1, wherein said mask has a chin portion that is configured to include at least a part of a chin of the user.

11. The mask according to claim 1, wherein said nasal interface consists of two nasal pillows.

12. The mask according to claim 11, wherein said pillows are connected to one another with a connecting member.

13. The mask according to claim 11, wherein said pillows have central axes tilted with respect to one another.

14. The mask according to claim 1, wherein:
    said nasal interface has a bottom end formed with rings defining at least one groove therebetween, said at least one groove having a given width; and
    said at least one orifice has an interior surface having a thickness for mating with said rings in a substantially gas-tight connection when said nasal interface is placed inside said at least one orifice.

15. A respiration assist mask comprising:
    a ventilation interface defining a gas entry port to be connected to a positive gas pressure source supplying a gas to said ventilation interface;
    a cushioned facial interface connected to said ventilation interface, said facial interface having:
        a gas exit shaped to substantially gas-tightly seal from the environment;
        a non-face contacting periphery comprised of a bottom wall, two side walls, and a top wall, wherein the top wall has an upper surface; and
        at least one orifice defined in said upper surface; and
    a nasal interface removably connected to said at least one orifice of said facial interface and adapted to be inserted within nares of the user to facilitate channeling said gas to the nares of the user, the nasal interface having a nasal interface gas exit that is external to the cushioned facial interface;
    wherein the cushioned facial interface is in fluid communication with the ventilation interface and the nasal interface.

16. The mask according to claim 15, wherein said ventilation interface comprises at least two walls extending about a periphery of said ventilation interface wherein a first wall is positioned a distance away from a second wall such that a groove is defined therebetween; and
    wherein said cushioned facial interface comprises an edge extending from said cushioned facial interface, said edge is sized and shaped to be positioned within said groove to facilitate removably coupling said cushioned facial interface to said ventilation interface.

17. A respiration assist mask comprising:
    a ventilation interface, said ventilation interface having:
        a gas entry port to be connected to a positive gas pressure source supplying a gas to said ventilation interface;
        a non-face contacting periphery comprised of a bottom wall, two side walls, and a top wall, wherein the top wall has an upper surface; and
        at least one orifice defined in said upper surface;
    a cushioned facial interface connected to said ventilation interface, said facial interface having a gas exit shaped to substantially gas-tightly seal from the environment; and
    a nasal interface removably connected to said at least one orifice of said ventilation interface and adapted to be inserted within nares of the user to facilitate channeling said gas to the nares of the user, the nasal interface having a nasal interface gas exit that is external to the cushioned facial interface;
    wherein the cushioned facial interface is in fluid communication with the ventilation interface and the nasal interface.

18. The mask according to claim 17, wherein said facial interface is made of a gel material.

* * * * *